US006633780B1

(12) United States Patent
Berger (10) Patent No.: US 6,633,780 B1
(45) Date of Patent: Oct. 14, 2003

(54) CARDIAC SHOCK ELECTRODE SYSTEM AND CORRESPONDING IMPLANTABLE DEFIBRILLATOR SYSTEM (75) Inventor: Ronald D. Berger, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 73 days.

(21) Appl. No.: 09/586,787

(22) Filed: Jun. 5, 2000

Related U.S. Application Data
(60) Provisional application No. 60/137,919, filed on Jun. 7, 1999.

(51) Int. Cl.[7] .................................................. A61N 1/05
(52) U.S. Cl. ........................ 607/129; 607/5; 607/148; 607/119
(58) Field of Search ................................. 607/4, 5, 119, 607/129, 130, 148

(56) References Cited

U.S. PATENT DOCUMENTS

| 4,030,509 | A | | 6/1977 | Heilman et al. |
| 4,564,812 | A | | 1/1986 | Van DIJK |
| 4,641,656 | A | * | 2/1987 | Smits ........................ 607/122 |
| 4,662,377 | A | | 5/1987 | Heilman et al. |
| 4,749,895 | A | | 6/1988 | Ruelle |
| 5,033,032 | A | | 7/1991 | Houghtaling |
| 5,133,365 | A | | 7/1992 | Hell, Jr. et al. |
| 5,344,430 | A | * | 9/1994 | Berg et al. ....................... 607/7 |
| 5,362,353 | A | | 11/1994 | Mallon |
| 5,456,706 | A | | 10/1995 | Pless et al. |
| 5,533,958 | A | | 7/1996 | Wilk |
| 5,594,200 | A | | 1/1997 | Ramsey |
| 5,645,572 | A | | 7/1997 | Kroll et al. |
| 5,761,053 | A | | 6/1998 | King et al. |
| 5,782,873 | A | | 7/1998 | Collins |
| 5,824,028 | A | * | 10/1998 | Knisley ........................ 607/129 |
| 5,944,746 | A | | 8/1999 | Kroll |
| 6,067,471 | A | | 5/2000 | Warren |
| 6,076,013 | A | * | 6/2000 | Brennan et al. ................. 607/2 |
| 6,169,922 | B1 | * | 1/2001 | Alferness et al. ........... 607/129 |

* cited by examiner

Primary Examiner—George R. Evanisko
(74) Attorney, Agent, or Firm—Nixon & Vanderhye P.C.

(57) ABSTRACT

An implantable cardioverter defibrillator (ICD) system includes an internal electrode placed in the right ventricle of the heart, and a flexible array (that includes a plurality of electrodes) placed over a significant portion of the heart. Defibrillation shocks are applied between the internal electrode in the ventricle and the electrodes in the flexible array. Because the electrodes in the flexible array surround a significant portion of the heart, the array functions as a quasi-Faraday cage and is thus capable of confining a significant portion of the defibrillation shock field to the heart itself. As a result, defibrillation shocks are less likely to activate extracardiac muscle(s) and/or nerve tissue(s) within the surrounding chest. Application of the shocks is thus less painful to the patient.

4 Claims, 6 Drawing Sheets

CARDIAC SHOCK ELECTRODE SYSTEM AND CORRESPONDING IMPLANTABLE DEFIBRILLATOR SYSTEM

This application is based upon United States Provisional Patent Application Serial No. 60/137,919, filed Jun. 7, 1999, the entire disclosure of which is hereby incorporated herein by reference and upon which priority is hereby claimed.

This invention relates to an implantable cardioverter defibrillator (ICD) system. In particular, this invention relates to a flexible array including a plurality of electrodes which may be selectively coupled to one another, for use in an ICD system.

BACKGROUND OF THE INVENTION

Many people die yearly from sudden cardiac death. In the vast majority of these cases, the cause of death is ventricular tachycardia and/or ventricular fibrillation. Automatic implantable cardioverting/defibrillating devices have been developed and shown to be effective in preventing sudden cardiac death from these causes.

Cardioversion (performed by a cardioverter) may be defined as the correction of either ventricular tachycardia or ventricular fibrillation by the discharge of electrical energy (e.g., shock) into the heart. The shock may be either synchronized or non-synchronized. Ventricular tachycardia is an abnormally rapid heart rate (120–240 beats per minute) originating in the heart's main pumping chambers (ventricles) which is regular in periodicity and often is life threatening to the patient. Ventricular fibrillation is generally a more rapid heartbeat disorder, disorganized and irregular, or non-periodic, and is often fatal unless corrected within minutes by the discharge of electrical energy through the heart. Sometimes, cardioversion may include delivery of an electric shock to the heart to correct ventricular tachycardia. Defibrillation may likewise include the non-synchronized delivery of electrical energy to the heart to correct ventricular fibrillation.

Figure 1:
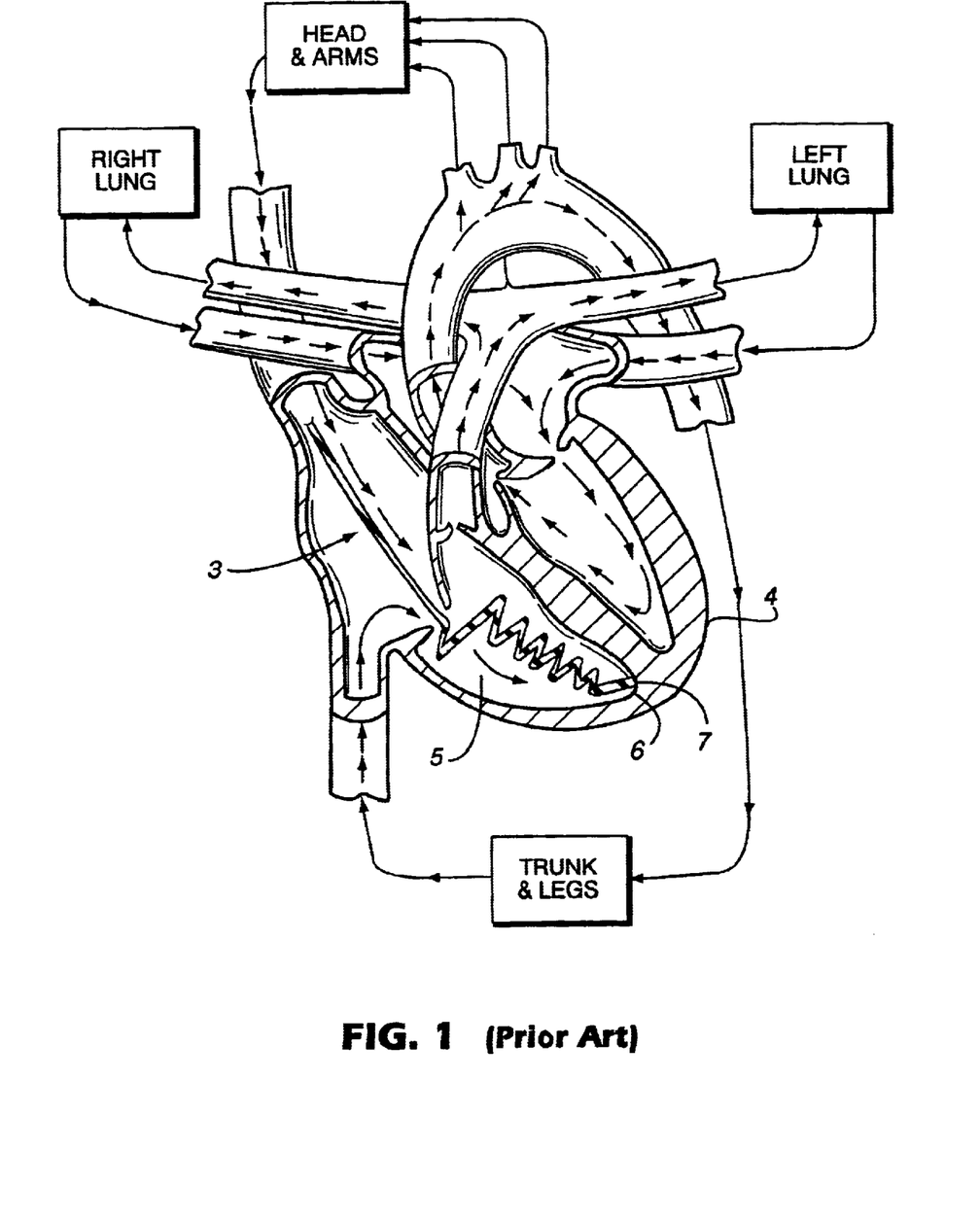
FIG. 1 is a partial cross-sectional view and partial schematic diagram of a conventional ICD system in which an internal electrode is placed in the right ventricle of a patient's heart.

A plurality of different types of implantable cardioverter defibrillation (ICD) systems are known in the art. For example, see each of U.S. Pat. Nos. 4,030,509; 4,662,377; 5,133,365; and 6,067,471; the disclosures of which are all hereby incorporated herein by reference. ICD systems may be used to provide electric shock to the heart in order to correct ventricular fibrillation. FIG. 1 illustrates an internal lead 3 of a conventional ICD system placed in the right ventricle 5 of a patient's heart 4. The distal tip electrode 6 is located in the right ventricular apex 7. Labeled boxes in the figure illustrate the directions in which blood is pumped throughout the body by the heart. Additional details of the FIG. 1 system are described in the aforesaid '365 patent.

Unfortunately, use of ICD systems may often be painful to the patient to which the shock is applied. A reason for this is that defibrillation shocks often extend beyond the heart and activate extracardiac muscle(s) and/or nerve tissue(s) within the peripheral chest area(s). Excessive pain is not desirable.

It will thus be apparent to those skilled in the art that there exist a need for an ICD system and/or method that may be less painful to a patient than one or more conventional ICD systems and/or methods.

SUMMARY OF THE INVENTION

An object of this invention is to provide an implantable cardioverter defibrillator (ICD) system and/or method that is less painful to a patient than one or more conventional ICD systems/methods.

Another object of this invention is to provide a flexible array including a plurality of electrodes for surrounding at least a portion of the heart, for use in an ICD system/method. In certain embodiments, individual electrodes in the array are selectively coupled to one another so that the electrodes may be electrically floating relative to one another during certain modes of ICD operation (e.g., heart monitoring modes) and electrically coupled to one another in other modes of ICD operation (e.g., shock modes).

Another object of this invention is to utilize the flexible array described above in a manner such that when the individual electrodes are electrically coupled to one another, a type of Faraday cage (e.g., "quasi-Faraday cage") is formed around a portion of the heart. This quasi-Faraday cage at least partially (or even fully in certain embodiments) confines the defibrillation shock field to the heart itself so that the shock does not activate extracardiac muscle(s) and/or nerve tissue(s) in the surrounding chest. This enables the ICD system and/or method to be less painful than one or more certain conventional ICD systems/methods.

Another object of this invention is to provide a selectively activatable Faraday cage, or quasi-Faraday cage, for use in ICD systems, or any other type of system including but not limited to non-medical applications.

Yet another object of this invention is to fulfill one or more of the aforesaid needs and/or objects.

In certain embodiments of this invention, an ICD system includes an internal electrode placed in the right ventricle of the heart, and a flexible array (that includes a plurality of electrodes) placed over a significant portion of the heart. Defibrillation shocks are applied between the internal electrode in the ventricle and the electrodes in the flexible array. Because the electrodes in the flexible array surround a significant portion of the heart, the array functions as a quasi-Faraday cage and thus is capable of confining a significant portion of the defibrillation shock field to the heart itself. As a result, defibrillation shocks do not activate extracardiac muscle(s) and/or nerve tissue(s) within the surrounding chest. Thus, application of the shocks is less painful.

DETAILED DESCRIPTION OF CERTAIN EMBODIMENTS OF THIS INVENTION

Referring now more particularly to the accompanying drawings in which like reference numerals indicate like parts throughout the several views.

Figure 2:
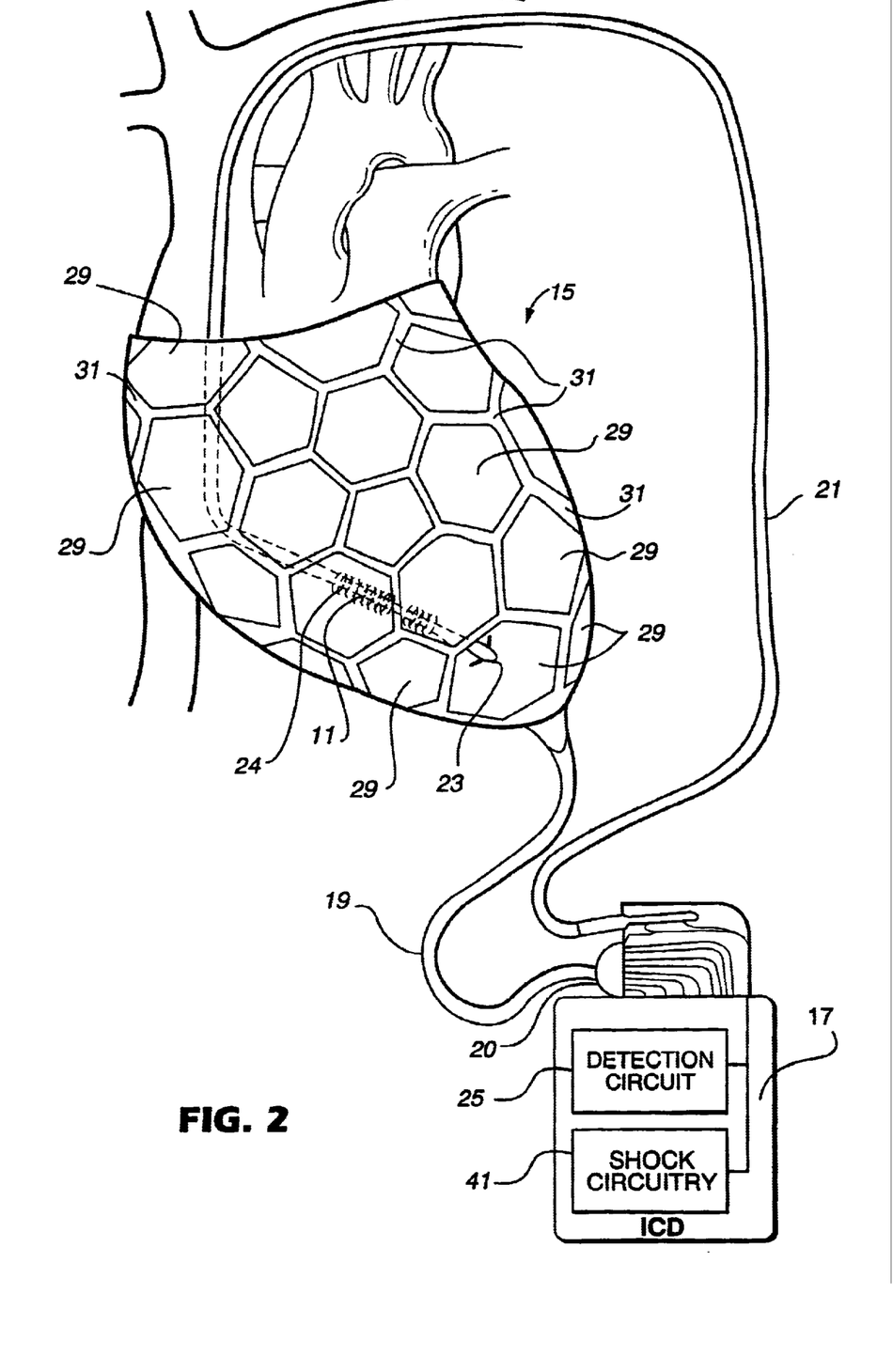
FIG. 2 is a front plan view of an ICD system according to an embodiment of this invention.

FIG. 2 illustrates an implantable cardioverter defibrillator (ICD) system according to an embodiment of this invention. The ICD system includes internal electrode or lead 11 provided within the heart (e.g., within the right ventricle), flexible array 15 (or flexible member) including a plurality of electrodes 29 surrounding a significant portion of the heart, ICD housing 17 to be implanted within the body at a location external the heart, and respective electrical leads 19 and 21 for interconnecting electrodes 29 and internal lead/electrode 11, respectively, with ICD housing 17. The ICD device includes housing 17, within which are located detection circuit 25 for monitoring the heart and determining when a defibrillating shock is needed and shock circuit 41 for causing the shock to be applied to the patient's heart via electrodes 11 and 29. The ICD system shown in the figures may be used, for example, for treatment of ventricular fibrillation, ventricular tachycardia, and/or atrial fibrillation. Additionally, the electrodes 29 may be used for pacing to alter ventricular activation sequence and improve cardiac function.

Internal electrode/lead 11 may be any type of conventional ICD lead. For example, see any and/or all of the internal leads of U.S. Pat. Nos. 4,662,377; 5,133,365; and/or 6,067,471, the disclosures of which are all hereby incorporated herein by reference. For example, lead/electrode 11 may include a distal tip electrode 23 to enable detection circuit 25 in the external ICD device to sense/detect ventricular endocardial activity and/or ventricular pacing in the heart. The lead 11 may further include a coil electrode 24 used in application of shock to the heart. In other words, in certain exemplary embodiments lead 11 may include two separate electrode portions, tip electrode 23 and coil electrode 24. It is noted, however, that electrodes 23 and 24 are for purposes of example only, and are not intended to be limiting. Any suitable type of electrode(s) may be utilized on or in conjunction with lead 11 in different embodiments of this invention.

Figure 3:
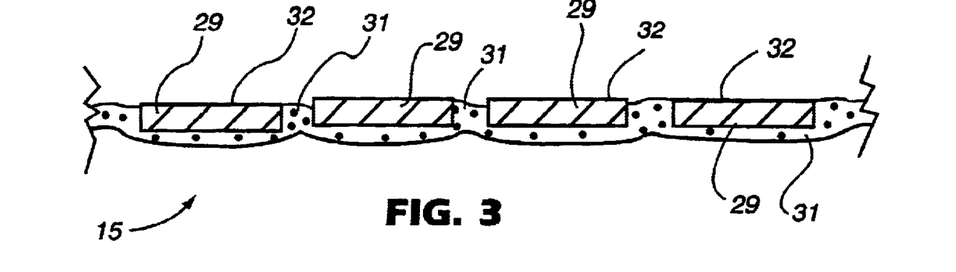
FIG. 3 is a cross-sectional view of a portion of the flexible array used in the FIG. 2 embodiment.
Figure 4:
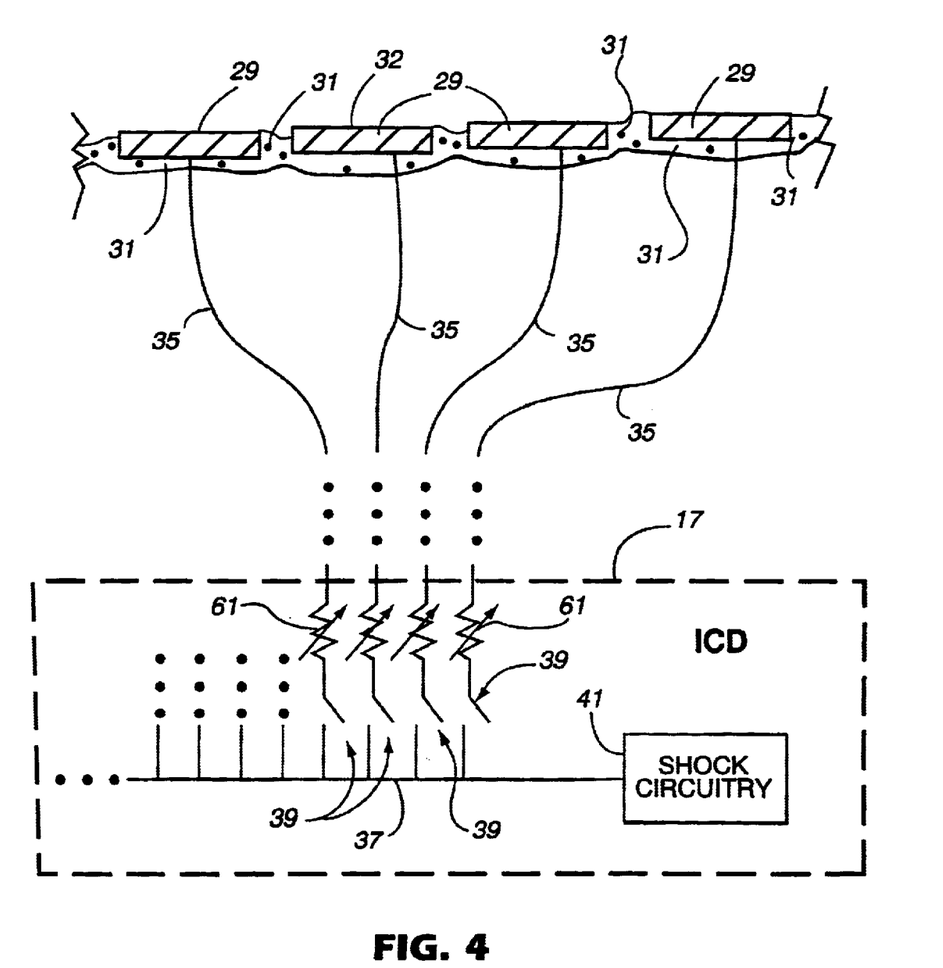
FIG. 4 is a schematic diagram illustrating that the electrodes in the array of FIG. 3 may be selectively coupled and decoupled to/from one another in different modes of operation of the ICD system of FIG. 2.

Referring to FIGS. 2 and 3, the flexible array 15 surrounds a portion of the heart, including a portion of the heart in which internal lead/electrode 11 is located. The flexible array 15 includes a plurality of different conductive electrodes 29 as well as insulating material 31 provided between the electrodes 29. Electrodes 29 may be of or include any conductive material, such as copper (Cu), indium-tin-oxide (ITO), chromium (Cr), Mb, Al, Fe, or any other suitable conductive material. As illustrated in FIGS. 2–3, insulating material 31 is provided between individual electrodes 29 in the array 15 so as to electrically insulate them from one another. Optionally, insulating material 31 may also be provided so as to surround portion(s) of each electrode 29 as shown in FIG. 3. However, in preferred embodiments, the side 32 of each electrode 29 that is to contact or be closest to the heart is not covered with material 31, as illustrated in FIGS. 3–4. Optionally, in certain embodiments the insulating material 31 is provided over the other side of each electrode 29. In certain embodiment of this in invention, insulating material 31 may be of or include a flexible fabric material such as cotton, nylon, or any suitable polymer based material. In other embodiments of this invention, insulating material 31 may be of or include a flexible polymer based non-fabric material that allows flexibility of the array 15. In preferred embodiments, insulating material 31 is also stretchable/elastic. The provision of insulating material 31 between adjacent electrodes 29 in array 15 enables the electrodes 29 to be electrically insulated from one another during certain modes of operation of the ICD system. In other modes of operation, to be described in more detail below, electrodes 29 may be electrically coupled to one another in order to form a quasi-Faraday cage which enables use of the ICD system to be less painful to the patient. The concept of a Faraday cage is known in the art; for example see U.S. Pat. Nos. 4,564,812, 5,362,353, 4,749,895, and 5,761,053, the disclosures of which are hereby incorporated herein by reference.

In order to implement certain embodiments of the instant invention, internal lead/electrode 11 may be placed transvenously in the heart (e.g., in the right ventricle as illustrated in FIG. 2), and the flexible array 15 (which may also be referred to as a flexible sock herein) may be placed over at least a portion of the heart via a limited thoracotomy. A hand-held tool may be used to deploy the flexible member 15 over the heart from the apex to base of the heart, allowing placement of the electrode 29 system on the outer surface of the heart. The array/sock 15 may be made of stretchable material that can conform to the cardiac external surface over which the array/sock 15 is placed. An expandable tool may be used to engage the opening of the array/sock 15 and facilitate application of the array/sock over the cardiac surface via a limited (sub-xiphoid) thoracotomy. The array/sock 15 may be advanced from the apex to the base of the patient's heart, covering most or all of the heart except the posterior atria and the outflow tracts of the great vessels beyond the pulmonic and aortic valves. In certain embodiments of this invention, flexible array/sock 15 (including electrodes 29 and insulating material 31) may surround or encompass at least about 50% of the heart, more preferably at least about 60%, and most preferably at least about 70%.

Defibrillation shocks are applied between the internal electrode (e.g., via coil electrode 24) and the plurality of electrodes 29 of the flexible array 15. Because electrodes 29 are electrically coupled to one another during application of defibrillation shocks, the array 15 functions as a quasi-Faraday cage thereby confining significant portions of the defibrillation shock field to the heart itself. The array 15 is said to form a "quasi"-Faraday cage because it surrounds only a portion of the heart (i.e., blood vessels must be permitted to extend through gaps or openings in the cage formed by array/sock 15).

Due to the provision of array 15 and its functionality as a quasi-Faraday cage during shock applications, the shocks applied to the heart via electrodes 24 and 29 are less likely to activate extracardiac muscle (s) or nerve tissue (s) within the surrounding chest area, so that the shock application via the illustrated ICD system is less painful.

Although implementation of certain embodiments of this invention may require more surgery than needed with existing ICD systems, the desire for less painful defibrillation is attractive for many. Moreover, at least partially surrounding the heart with array/sock 15 and at least partially confining the shock to the heart itself provides the potential for substantial reduction in the defibrillation energy threshold, and thus the prospect for ICD size reduction becomes real and/or achievable.

Figure 5:
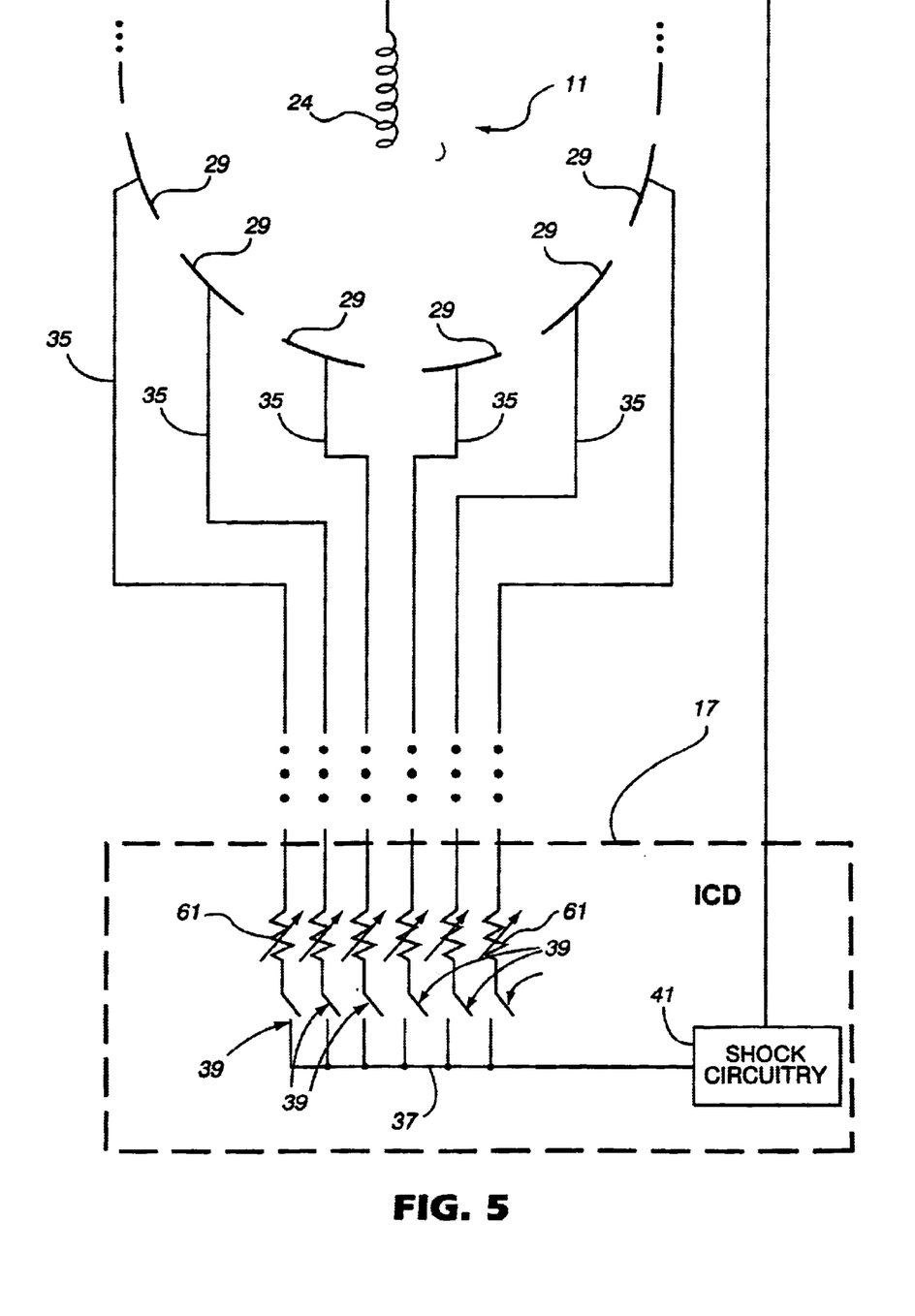
FIG. 5 is a circuit diagram illustrating circuitry enabling electrodes in the array of FIGS. 2–4 to be selectively coupled/decoupled to/from one another in different modes of operation of the ICD system of FIG. 2.

Referring to FIGS. 4–5, electrodes 29 of the flexible array 15 are electrically isolated (i.e., floating) from one another during modes of operation of the ICD system when shock is not being applied to the heart (e.g., when detecting circuit 25 is monitoring the heart). Electrodes 29 can be isolated from one another due to their respective spacings from one another and the provision of insulating material 31 therebetween. This electrical isolation of the electrodes 29 from one another enables native cardiac electrical activity to be measured at the body surface via a standard electrocardiogram (ECG). Such isolation also allows for the delivery of external defibrillation shocks (e.g., from the body's surface via conventional paddles) from which the heart would otherwise be largely shielded if the Faraday cage remained intact at all times.

However, when it is determined that defibrillation shock needs to be applied to the patient's heart in order to correct ventricular fibrillation, the electrodes 29 of flexible array/sock 15 are electrically coupled to one another prior to application of the shock. As shown in FIG. 4, each electrode 29 in array 15 has a conductive lead 35 extending therefrom back toward ICD housing 17 (leads 35 may extend through material 31 in the sock in certain embodiments until reaching cable 19). Each conductive lead 35 is selectively coupleable to an interconnecting bus 37 via a switch 39. Each of the plurality of switches 39 may be, for example, a relay, a switching transistor, or any other type of suitable switching element. When switches 39 are open (as shown in FIGS. 4–5), electrodes 29 are electrically isolated from one another. However, when switches 39 are closed, electrodes 29 become electrically coupled to one another so that the flexible array 15 forms a quasi-Faraday cage around a significant portion of the heart. Thus, it is said herein that the electrodes 29 are selectively coupleable to one another, so that the quasi-Faraday cage of array 15 may be selectively activated. In preferred embodiments of this invention, all switches 39 are in the same state at approximately the same time (i.e., switches 39 are either all open or all closed).

Still referring to FIGS. 4–5, after electrodes 29 of array 15 have been electrically coupled to one another by closing of switches 39, shock circuit 41 in the external ICD device causes defibrillation shock to be applied to the heart between internal electrode 24 and electrodes 29 of array/sock 15. This shock may be applied, for example, by providing a positive voltage potential on one electrode (24) and a negative voltage potential on the opposing electrodes (29), or vice versa. The provision of the quasi-Faraday cage formed by array 15 when electrodes 29 are electrically coupled substantially limits the shock to the heart itself, as the shock field is less likely to activate peripheral muscle(s) and/or nerve tissue(s) within the chest. Less pain is thus felt by the patient during application of the shock.

After the shock has been applied, switches 39 are preferably opened so that electrodes 29 are electrically decoupled from one another so that they are again floating or isolated. Thus, after electrodes 29 again become electrically isolated from one another, ECG measurements may be taken and/or external defibrillation shocks may be applied. The opening/closing of switches 39 is preferably controlled by shock circuitry 41 provided in housing 17, or alternatively can be controlled by a controller (e.g., CPU or other type of processor) provided within housing 17 of the external ICD device.

Figure 6:
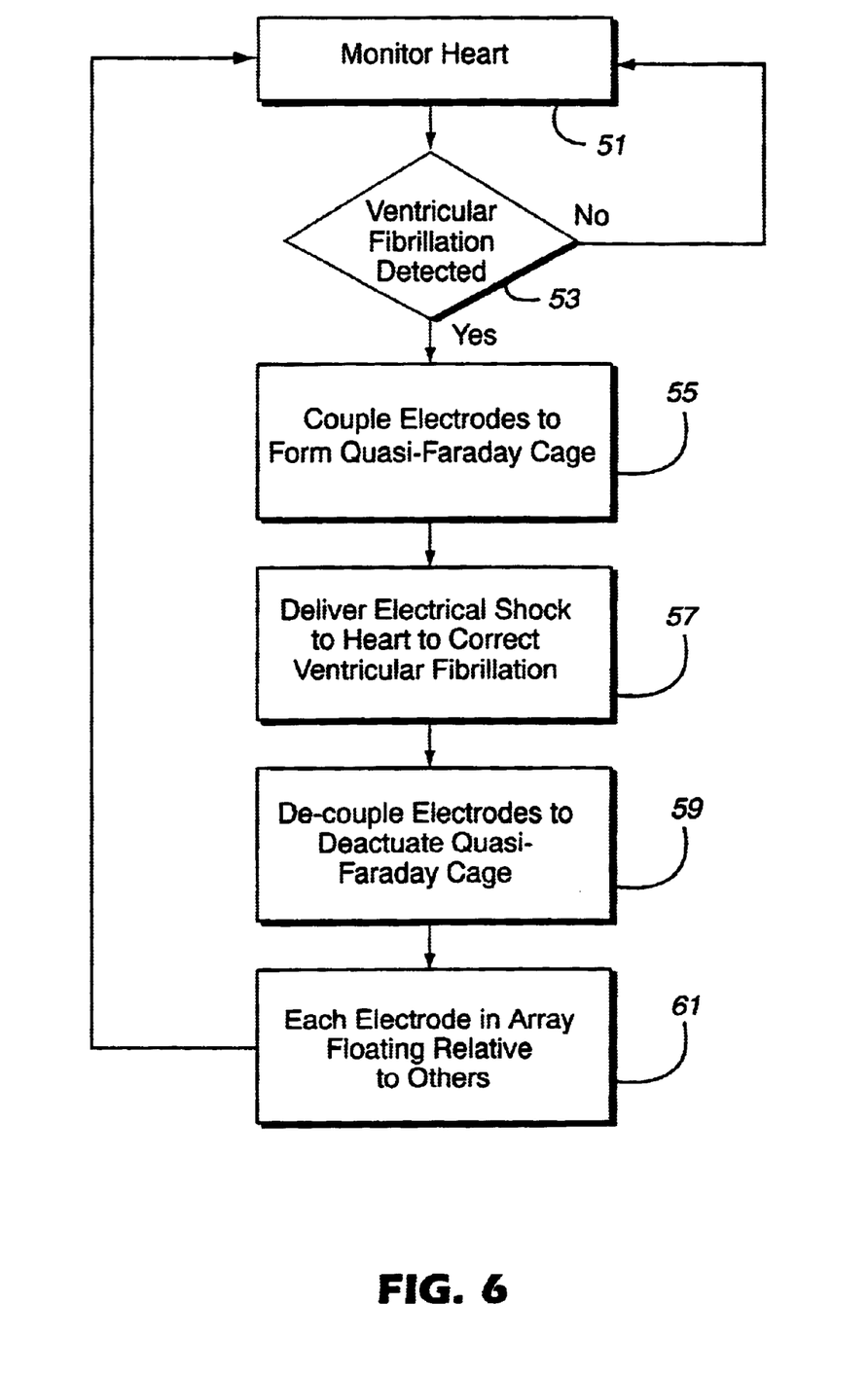
FIG. 6 is a flow chart illustrating certain steps taken during implementation of a method corresponding to the FIGS. 2–5 embodiment of this invention.

FIG. 6 is a flowchart illustrating certain steps taken during a process of implementing an embodiment of this invention. Detection circuit 25 in ICD housing 17 monitors the heart at step 51. Circuit 25 determines at step 53 whether or not ventricular fibrillation is detected. If not, the system continues to monitor the heart at step 51. However, if ventricular fibrillation is detected, switches 39 are closed at step 55 so as to electrically couple electrodes 29 of flexible array 15.

The quasi-Faraday cage is thus formed around a significant/substantial portion of the heart. After formation of the cage, the ICD system delivers electrical shock to the heart at step 57 in order to correct ventricular fibrillation. As discussed above, this shock may be applied between internal electrode 11 and electrodes 29. After the shock has been applied in step 57, switches 39 are opened at step 59 in order to decouple electrodes 29 from one another. The quasi-Faraday cage is thus deactivated. Thereafter, at step 61, each electrode 29 in the array 15 is electrically isolated from the other electrodes in the array as the ICD system monitors the heart at 51.

Various geometric arrangements of electrodes 29 are possible. In certain embodiments, a combination of hexagon shaped electrodes and pentagon shaped electrodes may be utilized (i.e., as on the surface of a soccer ball) as these shapes fit together and fill a substantial portion of the surface area of the array. In other embodiments, electrodes 29 may be shaped in the form of circles, ovals, rectangles, triangles, or any other suitable shape.

Referring to FIGS. 2–5, ICD device 17 is configured to work in conjunction with the illustrated lead system. Lead/cable 19 from flexible array/sock 15 includes wires 35, with one wire 35 preferably provided for each electrode 29 in the array. A multiple pin connector 20 may be utilized for connecting cable 19 to the ICD device. As discussed above, the ICD device includes switching circuitry (a CPU and/or shock circuit 41) for electrically joining the electrodes 29 during shock delivery and isolating them at other times. Far-field electrogram storage may be obtained between desired electrodes 29, or between the internal coil 24 and any desired electrode 29, in certain embodiments.

Referring to FIGS. 4–5, in certain embodiments of this invention variable resistors 61 (e.g., selectively variable or programmable resistors) may optionally be provided within ICD device 17. As illustrated, one such resistor 61 may be provided in series or in line with a corresponding electrode 29 in the flexible array. Adjustment of resistors 61 permits adjustment of current density and/or flow during defibrillation shocks within the quasi-Faraday cage so as to reduce the defibrillation threshold, and/or reduce shunting of current between coil 24 and one or more of electrodes 29. In preferred embodiments of this invention, the resistance of elements 61 is kept at a small value(s) so that the integrity of the quasi-Faraday cage is not lost. In embodiments including variable resistors 61 as shown in FIGS. 4–5, the value of each resistor 61 may either be programmed in advance, or alternatively the resistance value(s) may adjusted by shock circuit 41 or a CPU within the ICD device.

Production of a more radially symmetric shock field within the heart may require positioning an internal coil electrode 24 as centrally within the heart as logistically possible. This may entail passively or actively fixuating the internal lead 11 to the mid-septal region of the right ventricle.

Figure 7:
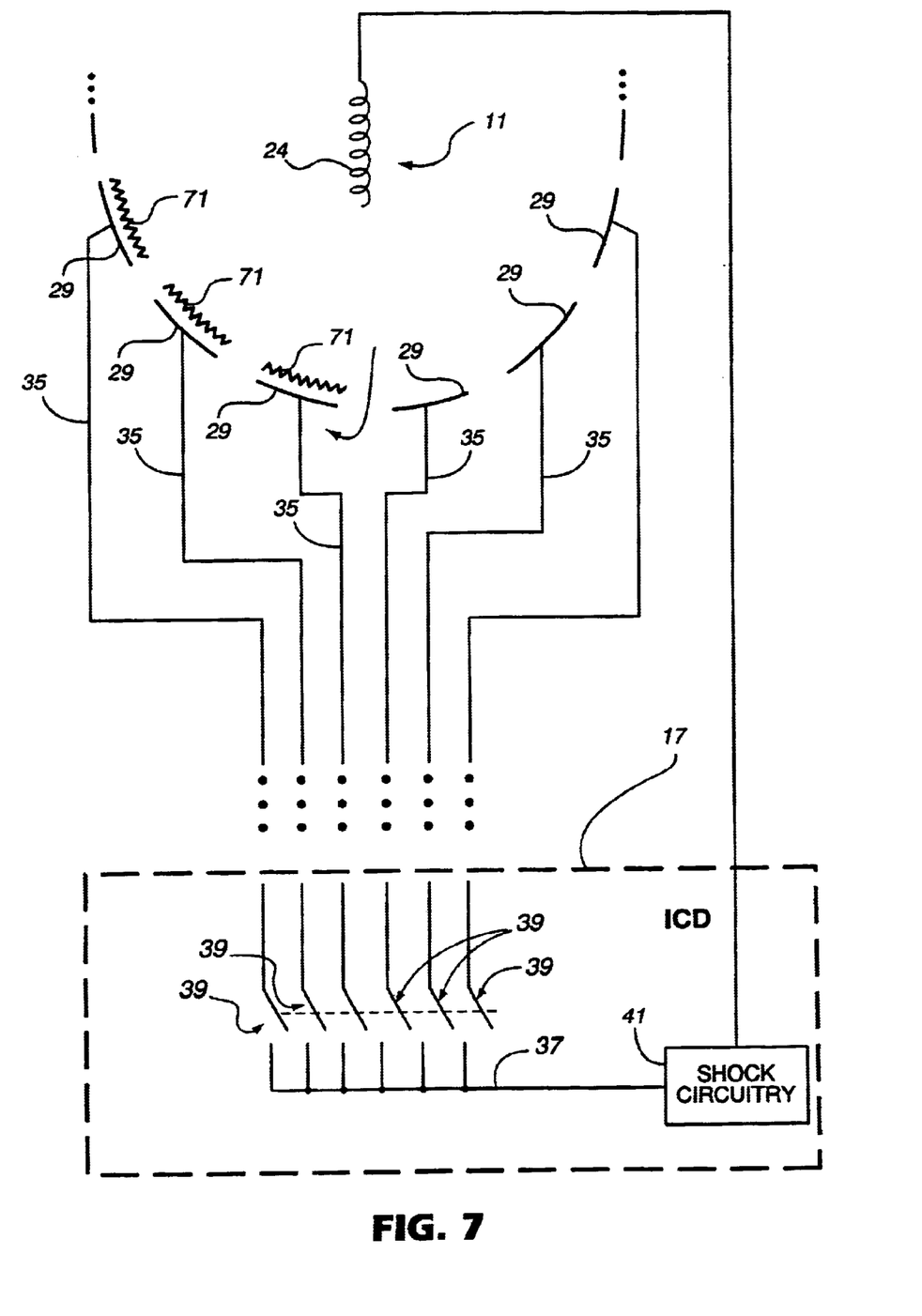
FIG. 7 is circuit diagram illustrating another embodiment of this invention, which differs from the FIG. 5 embodiment in that resistive pads/elements are provided in the flexible array so that different current densities may be applied to different areas of the heart.

FIG. 7 illustrates another embodiment of this invention, that differs from that of FIGS. 4–5 in that variable resistors 61 are not provided within device 17. Instead, the resistance associated with one or more electrodes 29 may be adjusted by use of resistive pads or other resistive elements 71 provided in the array itself. Resistive pads/elements 71 of different resistance values may be electrically coupled to different electrodes 29 within the array. Elements 71 may have fixed or variable resistance(s) in different embodiments. Some electrodes 29 may not have resistive pads 71 coupled thereto. The purpose in this embodiment is the same as in the FIGS. 4–5 embodiment. Different current densities may be applied to different areas of the heart. This may be desirable in different types of defibrillation shock applications.

In still further embodiments of this invention, electrodes 29 of flexible array 15 may be used as a passive quasi-Faraday cage shield and need not be used for application of the actual shock to the heart. In such embodiments, first and second internal coil electrodes 24 (only one of which is shown in the figures) are placed within the heart and used to complete the shock delivery circuit from the ICD device. As in the previous embodiments, electrodes 29 remain electrically isolated from one another until it is time to deliver the shock to the heart. At this time, switches 39 are closed in order to form the quasi-Faraday cage. While the electrodes 29 in array 15 are not an active part of the shock circuitry in such embodiments, the presence of the quasi-Faraday cage again prevents activation of extracardiac tissue so that the shock is less painful to the patient. An example where this embodiment may be useful is in atrial defibrillation (or any other suitable application), where shock electrodes may be placed within the right atrium and coronary sinus.

Yet another advantage associated with certain embodiments of this invention is that the flexible member 15 when placed around a significant portion of the heart presses up against the heart (i.e., squeezes heart muscle) so as to improve cardiac function and reduce heart failure symptoms. Thus, the ICD system may function both in an ICD manner as described herein, and additionally may also function in a squeezing manner to improve cardiac function.

It is further emphasized that the illustrations herein are for purposes of example only and are not intended to be limiting. For example, lead 11 and/or electrode 24 may be placed at locations within the heart other than those illustrated herein. Moreover, array/sock 15 may also be provided at other location, or may be provided so as to surround a different portion of the heart in alternative embodiments of this invention. Finally, it is noted that selectively activateable quasi-Faraday cages (or even selectively activateable full Faraday cages) in accordance with embodiments of this invention may have application (i.e., use) in non-medical application, or in medical applications other than those described herein.

Once given the above disclosure, various other modifications, features, and/or improvements will become apparent to the skilled artisan. Such other features, modifications, and/or improvements are thus considered to be a part of this invention, the scope of which is to be determined by the following claims

What is claimed is:

1. An implantable cardioverter defibrillator (ICD) system for applying electric shock to a heart of a patient in a shock applying mode, the ICD system comprising:
    an internal electrode adapted to be placed inside of the heart of the patient;
    a quasi-Faraday cage including a plurality of different electrodes, so that the electric shock is to be applied between the quasi-Faraday cage which is adapted to be located outside of the heart and the internal electrode adapted to be placed inside of the heart;
    wherein said electrodes of the quasi-Faraday cage are adapted to be wrapped around at least about 50% of the heart during application of the electric shock so as to confine a significant portion of a defibrillation shock field to the heart itself so as to prevent the shock from significantly stimulating extracardiac muscle(s) and/or nerve(s) tissue;
    switching circuit; and
    wherein said electrodes of said quasi-Faraday cage are selectively coupleable to one another via said switching circuitry so that in a mode of operation of the ICD system where no shock is applied to the heart the electrodes of said quasi-Faraday cage are electrically isolated from one another, and in the shock-applying mode of the ICD system where shock is applied to the heart the electrodes of said quasi-Faraday cage are electrically coupled to one another via said switching circuitry so that the electric shock is adapted to be applied to the heart between (a) the internal electrode, and (b) the coupled electrodes of said quasi-Faraday cage so that application of the shock to a patient is less painful.

2. The ICD system of claim 1, further comprising insulating material provided between adjacent ones of said electrodes, and wherein said electrodes of said quasi-Faraday cage are in the form of an array of electrodes.

3. An implantable cardioverter defibrillator (ICD) system for applying electric shock to a heart of a patient, the ICD system comprising:
    an internal electrode adapted to be placed inside of the heart of the patient;
    switching circuit;
    a quasi-Faraday cage including a plurality of different selectively coupleable electrodes which are selectively electrically coupleable to one another via said switching circuitry, wherein the electric shock is adapted to be applied to the heart between (a) the internal electrode, and (b) the electrodes of the quasi-Faraday cage when the electrodes of the cage are electrically coupled via the switching circuitry; and
    wherein the electrodes of the quasi-Faraday cage surround at least about 70% of the heart during application of the electric shock so as to confine a significant portion of a shock field to the heart itself so as to prevent the shock from significantly stimulating extracardiac muscle(s) and/or nerve(s) tissue.

4. An implantable cardioverter defibrillator (ICD) system for applying electric shock to a heart of a patient, the ICD system having an internal electrode adapted to be placed inside of the heart of the patient, the ICD system comprising:
    a quasi-Faraday cage including electrodes;
    wherein electrodes of the quasi-Faraday cage are adapted to be wrapped around at least about 60% of the heart during application of the electric shock so that electric shock is adapted to be applied to the heart between the electrodes of the quasi-Faraday cage and the electrode of the ICD adapted to be located inside of the heart to make the shock less painful as a significant portion of a defibrillation shock field is confined to the heart itself so as to prevent the shock from significantly stimulating extracardiac tissue.

* * * * *